United States Patent [19]

Waycuilis

[11] Patent Number: 5,149,340
[45] Date of Patent: Sep. 22, 1992

[54] PROCESS AND APPARATUS FOR SEPARATING IMPURITIES FROM HYDROCARBONS

[75] Inventor: John J. Waycuilis, Lafayette, La.

[73] Assignee: Marathon Oil Company, Findlay, Ohio

[21] Appl. No.: 672,059

[22] Filed: Mar. 12, 1991

[51] Int. Cl.$^5$ .................... B01D 53/22; B01D 63/10
[52] U.S. Cl. .................................... 55/16; 55/68; 55/158
[58] Field of Search ......................... 55/16, 68, 158

[56] References Cited

U.S. PATENT DOCUMENTS

| | | | |
|---|---|---|---|
| 1,496,757 | 6/1924 | Lewis et al. | 55/16 |
| 2,947,687 | 8/1960 | Lee | 210/23 |
| 3,043,891 | 7/1962 | Stuckey | 260/674 |
| 3,339,341 | 9/1967 | Maxwell et al. | 55/16 |
| 3,624,983 | 12/1971 | Ward, III | 55/16 |
| 3,735,558 | 5/1973 | Skarstrom et al. | 55/16 |
| 3,735,559 | 5/1973 | Salemme | 55/16 |
| 3,770,842 | 11/1973 | Steigelmann et al. | 260/677 A |
| 3,800,506 | 4/1974 | Hughes et al. | 55/16 |
| 3,844,735 | 10/1974 | Steigelmann et al. | 55/16 |
| 3,865,890 | 2/1975 | Steigelmann et al. | 55/16 |
| 3,951,621 | 4/1976 | Hughes et al. | 55/16 |
| 4,060,566 | 11/1977 | Yahnke | 260/677 A |
| 4,386,944 | 6/1983 | Kimura | 55/16 |
| 4,659,343 | 4/1987 | Kelly | 55/16 |
| 4,670,151 | 6/1987 | Bitter | 210/641 |
| 4,718,921 | 1/1988 | Makino et al. | 55/16 |
| 4,834,779 | 5/1989 | Paganessi et al. | 55/16 |
| 4,857,081 | 8/1989 | Taylor | 55/16 |
| 4,931,070 | 6/1990 | Prasad | 55/16 |
| 4,961,759 | 10/1990 | Taylor | 55/16 |
| 4,973,434 | 11/1990 | Sirkar et al. | 55/16 X |
| 4,981,498 | 1/1991 | Bikson et al. | 55/16 |
| 5,034,025 | 7/1991 | Overmann, III | 55/16 |

*Primary Examiner*—Robert Spitzer
*Attorney, Agent, or Firm*—Jack L. Hummel; Jack E. Ebel

[57] ABSTRACT

A semi-permeable membrane process of separating impurities from a hydrocarbon mixture. A fuel gas sweep gas is used to purge and dilute the permeate. Because this reduces the partial pressure of the impurities, the driving force for permeation is increased even though the permeate mixture pressure is increased to the extent that the system need not employ a compressor or vacuum pump. The mixture of permeate, fuel gas and permeated hydrocarbon product can be delivered at a pressure sufficient to flow directly to the plant fuel system or other system for use therein. Specific membrane units employing hollow fiber membranes or spirally wound stacked membrane layers are disclosed.

4 Claims, 4 Drawing Sheets

PROCESS AND APPARATUS FOR SEPARATING IMPURITIES FROM HYDROCARBONS

FIELD OF THE INVENTION

This invention relates to a process for removing impurities from liquid hydrocarbons. More particularly, it relates to a process which utilizes semi-permeable membranes to separate impurities from liquid or gaseous hydrocarbon mixtures.

BACKGROUND OF THE INVENTION

In the processing of hydrocarbon fluids it is necessary to remove impurities such as carbon dioxide, water, sulfur compounds and other substances from hydrocarbon mixtures. Although various processes have been developed over the years to accomplish this, increased emphasis on less energy intensive processes is causing processes which may have been considered satisfactory in the past to be reexamined. Solvent processes utilizing amines are an example of one approach which is now perceived as requiring too much energy to operate. In addition, disposal of spent aqueous solvents presents an environmental burden.

An energy saving alternative to solvent processes and other processes for removing impurities from liquid or gaseous hydrocarbons is the use of semi-permeable membranes. The theory and use of semi-permeable membranes, also sometimes referred to in the art as permeable membranes, are well known. A feed stream of the hydrocarbon fluid to be treated is caused to contact, at elevated pressure, a membrane designed to selectively permit specific materials to pass through by diffusion. When the partial pressure of the material in question is sufficiently greater in the feed stream than on the permeate side of the membrane, permeation flux of the material to the lower partial pressure takes place. A problem arises when valuable hydrocarbons are lost in the permeate. In such cases a compressor is normally employed to capture or recycle the permeate or to repressurize the permeate for a second stage of permeation. In other cases, it is necessary to use vacuum pumps or compressors to produce sufficient driving force to effect the separation economically, or at all. Such arrangements substantially increase the capital cost of the process as well as the operating expense.

It would be beneficial to be able to eliminate the need for a compressor in the system, thereby reducing the costs mentioned above. It would also be beneficial to reduce costs by making the primary membrane smaller, without impairing the efficiency and effectiveness of the process.

BRIEF SUMMARY OF THE INVENTION

A process for separating gaseous impurities from a liquid or gaseous hydrocarbon mixture employs a membrane which is selectively permeable to the impurities desired to be separated from the mixture, with a flowing stream of the liquid or gaseous hydrocarbons contacting one side of the membrane. The impurities that permeate through to the other side of the membrane are purged by a stream of sweep gas flowing either countercurrent or crosscurrent to the direction of flow of the liquid hydrocarbon mixture to be purified. The stream of sweep gas dilutes the impurities on the permeate side of the membrane, at the same time reducing the partial pressure of the impurities, to thereby increase the driving force of the impurities across the membrane. The partial pressure of the impurities is decreased even though the use of sweep gas in this process causes and allows the total permeate back pressure on the permeable membrane to be increased.

In order to sufficiently reduce the partial pressure on the permeate side of the membrane to compensate for the higher total permeate pressure obtained, the ratio of the molar flow rate of the sweep gas to the molar permeation rate of the impurity removed from the hydrocarbon mixture depends on the pressure at which the permeate must be delivered, but typically should be at least 2 to 1. This ratio may be higher than 3 to 1 if there is a requirement such as for plant fuel to be supplied at pressures greater than 60 psig. The driving force for removal of the impurities is augmented despite the fact that the total permeate pressure is able to be increased to such an extent by this method that the need for a compressor in the fluid system is negated.

The membrane arrangement may be of any suitable design, so long as it allows the process to function in the manner described. For example, the membrane may be in the form of a plurality of cylinders or hollow fibers, with the space within the fibers receiving the sweep gas and permeate and the space between the exterior of the fibers and the wall of the container in which the membrane fibers are mounted receiving the hydrocarbon. In the foregoing arrangement the hollow fibers can be aligned substantially parallel to the direction of flow of the hydrocarbon mixture to be purified or transverse to the direction of flow.

Another alternative membrane arrangement utilizes spirally wrapped sheets of semi-permeable membrane, interleaved with alternating spacers to permit the flow of permeate on one side of a membrane sheet and the hydrocarbon to be purified on the other side. As explained more fully below, the construction of spirally wrapped membranes can be modified to facilitate the use of the sweep gas in this process in order to eliminate the need for a compressor without resorting to wasteful venting or flaring of the permeate.

Because the process permits removal of impurities by a membrane without employing a compressor or additional stages of impurity removal, the capital cost of the system is significantly reduced. By utilizing fuel gas as the sweep gas and introducing the mixture of the permeate and the sweep gas into the fuel system of the plant, the operating cost is further significantly reduced.

These benefits and the features of the invention which provide them are brought out in more detail in the following detailed description of the preferred embodiments, wherein the above and other aspects of the invention, as well as other benefits, will readily be apparent.

DETAILED DESCRIPTION OF THE PREFERRED EMBODIMENTS

Figure 1:
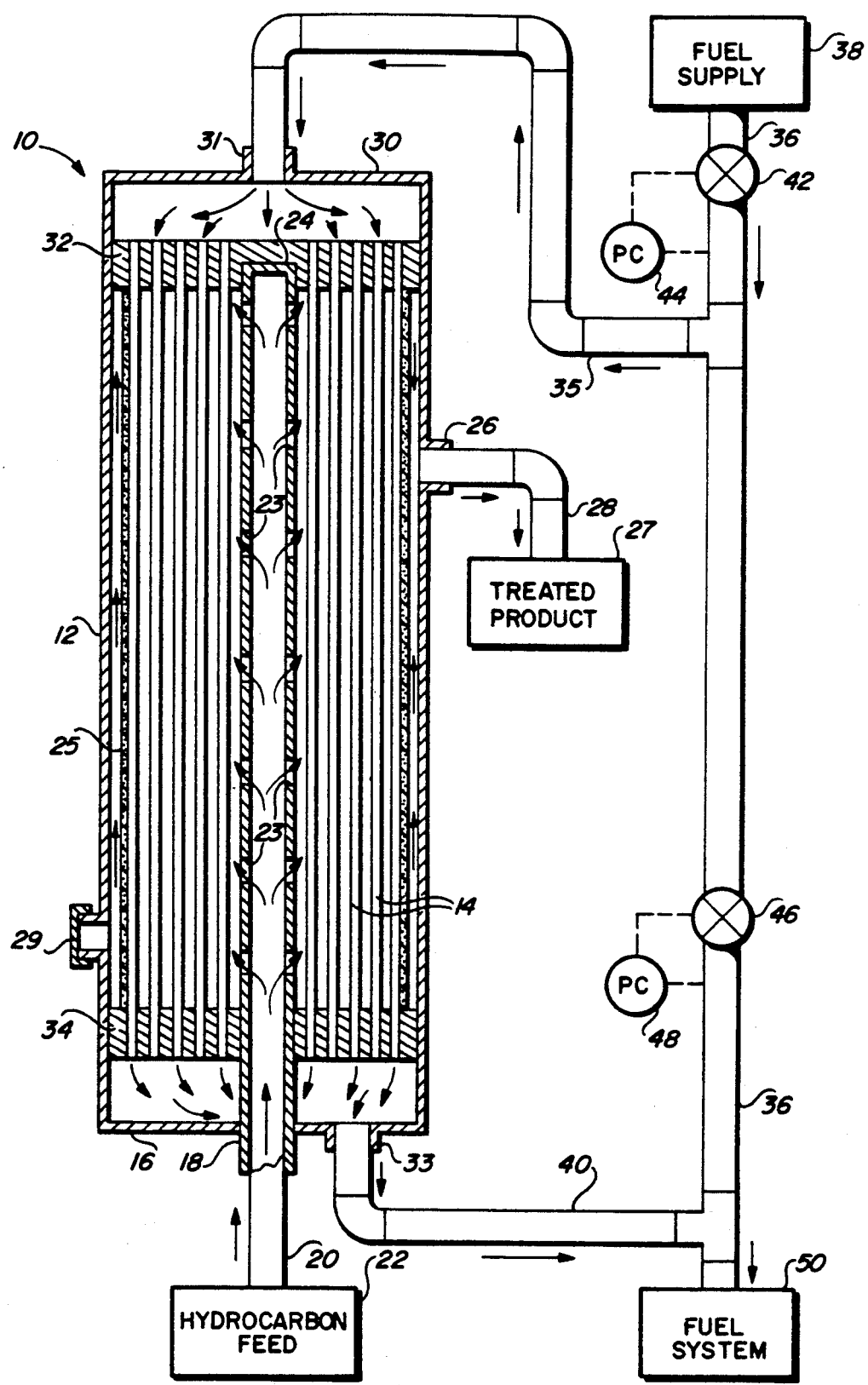
FIG. 1 is a longitudinal sectional view of a membrane unit or module incorporated in a schematically illustrated fluid system in which the process of the present invention is carried out.

Referring to FIG. 1, a membrane unit 10 is comprised of a cylindrical shell or container 12 in which a plurality of hollow fiber membranes 14 are mounted so as to extend longitudinally in the shell. An end wall 16 of the shell includes an inlet tube 1B to which a feed conduit 20 leading from a source 22 of hydrocarbons is connected by suitable means. The inlet tube 18 contains perforations 23 throughout its length and is sealed at the opposite end 24 so as to distribute hydrocarbon into the center of the bundle of hollow fiber membranes. The hydrocarbons typically include impurities, such as carbon dioxide, water, sulfur or others which it is desired to remove. The bundle of fibers is wrapped by a porous covering 25 through which fluid can flow and which prevents shifting of the fibers in the bundle. An outlet 26 in the container 12 is open to the annular space between the container wall and the porous covering 25 to provide an outlet for treated or purified hydrocarbon products. The treated hydrocarbon product is directed to another station 27 through fluid line 28 which is connected to the outlet 26. An alternate outlet 29, which is shown as being capped, may be used as a drain if desired.

The end wall 30 is provided with an inlet 31 which leads to the header space between the end wall 30 and disc 32, and the end wall 16 contains an outlet 33 leading from the header space between the end wall 16 and the disc 34. The disc 32 holds the ends of the hollow fibers 14 so that their open ends communicate with their associated header space, while the disc 34 holds the other ends of the fibers so that their open ends communicate with their associated header space. A conduit 35 connects the inlet 31 to a conduit 36 leading from a source 38 of pressurized fuel gas, enabling fuel gas to flow inside the hollow fibers 14, sweeping along the permeated impurities. A conduit 40 connects the outlet 33 to the conduit 36 downstream from the conduit 35. A valve 42 located in the line 36 upstream from the conduit 35 is controlled by a conventional pressure controller 44, which is set to maintain the pressure in the line at a predetermined level. A similar arrangement is provided downstream of the conduit 35 but upstream of the conduit 40, whereby a valve 46 maintains a predetermined lesser pressure at that point in accordance with the operation of the pressure controller 48. As illustrated, the conduit 36 leads to the fuel system 50 of the plant in which the treatment process is located.

In operation, a mixture of hydrocarbons and impurities is delivered to the container 12 through the feed inlet 18. The hydrocarbon mixture flows continuously through the perforations 3 and through the container, exiting through the outlet 26. While flowing through the container the hydrocarbon stream contacts the bundle of hollow fiber membranes 14 in radial cross-flow, permitting certain impurities in the stream to diffuse through the membrane wall. The theory and action of this selective permeation is well known in the art of so-called permeable or semi-permeable membranes and need not be described in more detail here. It should be understood that membranes or membrane modules which are designed to permit passage therethrough of the specific impurities normally desired to be removed from hydrocarbon substances are readily commercially available and need not be newly developed for use in carrying out this invention. Suitable membranes are available, for example, from Cynara Corporation of Houston, Tex. It will also be understood that even membranes specifically designed and selected to permit only certain gaseous ingredients of an impure hydrocarbon stream to permeate the membrane will nonetheless permit small amounts of liquid hydrocarbon to pass through in vapor form. While these amounts are small with respect to the volume of hydrocarbons in the product stream, they can be substantial in total amount if the volume of the stream passing through the membrane unit per unit of time is large.

Rather than simply vent the impurities (and hydrocarbon) or collect them from the permeate side of the membrane using a compressor or vacuum pump, as is typically done, fuel gas is supplied under pressure through the inlet 31 and removed through the outlet 33. In doing this, the valve 46 may be set to the minimum required plant fuel system pressure, while the upstream valve 42 is set to a higher pressure so as to regulate the flow of the fuel gas sweep across the membrane unit.

The introduction of sweep gas into the space within the membrane increases the back pressure on the permeate side of the membrane, which would normally be thought to be counterproductive to the passage of impurities from the hydrocarbon mixture through the membrane. In fact, however, the dilution of the permeate gases by the sweep gas actually reduces the partial pressure of the permeate constituents so that the difference in partial pressure from the feed side of the membrane to the permeate side is increased. The result of this is that the overall driving force, and hence the flux across the membrane, is increased significantly for the impurities but changed to a much lesser proportion for the hydrocarbon. Additionally, as the ratio of the molar flow rate of the sweep gas to the molar permeation rate of the impurities removed is increased, the partial pressure on the permeate side of the membrane is further reduced, thereby causing a greater driving force and permeation flux. Because the flux of the impurity is increased, the membrane area required for a given removal rate may be significantly reduced. Because the membrane area is reduced, however, the unwanted flux of the hydrocarbon liquid is also partially reduced, because the driving force for the hydrocarbon is not significantly changed. Thus, selectivity for the removal of the impurity is improved to an unexpected extent. Using this process, a separation as good as or better than the conventional process can be obtained with a reduced capital investment and operating expense due to the smaller membrane surface area and also due to elimination of a compressor. As stated previously, in order to sufficiently reduce the partial pressure on the permeate side of the membrane to compensate for the higher total permeate pressure obtained, the ratio of the molar flow rate of the sweep gas to the molar permeation rate of the impurity removed from the hydrocarbon mixture should be at least 2 to 1.

The phenomenon discussed which results in increased driving force, flux and selectivity can be demonstrated by a comparison of the theoretical driving forces across the membrane for a hypothetical typical liquid hydrocarbon mixture. Theoretical driving forces are calculated from the integral of the difference in partial pressures for a species across the membrane from one end of the device to the other, assuming countercurrent flow. The solution to this integral is the so-called log-mean difference. The figure used in computing the driving forces are illustrated in the following tables, wherein Tables 1A and 1B compare the hypothetical stream rates of a liquid feed, the treated product and the permeate in a conventional membrane unit which does not utilize a purging gas stream, to the hypothetical stream rates of a unit performing the same purification, functioning in accordance with the invention. Tables 2A and 2B compare the hypothetical partial pressures of the components in the stream in a conventional unit to the hypothetical partial pressures of the components in the stream in a unit which functions in accordance with the present invention.

TABLE 1A

Hypothetical Stream Rates. Mols per hr. Without Gas Sweep

| Component* | Feed | Treated Product | Permeate (outlet to compressor) |
|---|---|---|---|
| $C_1$ | 1 | 1 | 0 |
| $C_2$ | 89 | 87 | 2 |
| $CO_2$ | 10 | 5 | 5 |
| Total | 100 | 93 | 7 |

*$C_1$ = Methane
$C_2$ = Ethane (Product Hydrocarbon)
$CO_2$ = Carbon Dioxide (Impurity)

TABLE 1B

Hypothetical Stream Rates. Mols per hr. With Gas Sweep

| Component | Feed | Treated Product | Gas Sweep | Permeate (to fuel) |
|---|---|---|---|---|
| $C_1$ | 1 | 3 | 15 | 13 |
| $C_2$ | 89 | 87 | 0 | 2 |
| $CO_2$ | 10 | 5 | 0 | 5 |
| Total | 100 | 95 | 15 | 20 |

TABLE 2A

Stream Partial Pressures, psia, Without Gas Sweep

| Component | Feed | Treated Product | Permeate (Inlet) | Permeate (Outlet) |
|---|---|---|---|---|
| $C_1$ | 10.15 | 10.90 | 0 | 0 |
| $C_2$ | 903.35 | 948.58 | 8.57 | 4.286 |
| $CO_2$ | 101.50 | 54.52 | 21.43 | 10.714 |
| Total | 1015.00 | 1014.00 | 30.00 | 15.00 |

The theoretical driving forces for components $C_2$ and $CO_2$ as calculated as the log-mean partial pressure differences from the above figures are approximately 919 psia and 60 psia, respectively.

TABLE 2B

Stream Partial Pressures, psia, With Gas Sweep

| Component | Feed | Treated Product | Gas Sweep | Permeate Mixture (to fuel) |
|---|---|---|---|---|
| $C_1$ | 10.15 | 32.02 | 105.00 | 48.75 |
| $C_2$ | 903.35 | 928.61 | 0 | 7.50 |
| $CO_2$ | 101.50 | 53.37 | 0 | 18.75 |
| Total | 1015.00 | 1014.00 | 105.00 | 75.00 |

The theoretical log-mean partial pressure difference driving forces for the product hydrocarbon and $CO_2$ as computed from the above figures are approximately 912 psia and 67 psia, respectively. Thus the driving force for the removal of $CO_2$ was increased by approximately 12%, while the driving force causing the loss of $C_2$ in the product hydrocarbon was not appreciably changed (but in fact, actually decreased by 1% in this example due to the reverse permeation of a small amount of methane). As mentioned above, as the ratio of molar flow rate of the fuel gas sweep to the molar permeation rate of the impurity removed from the hydrocarbon product mixture is still further increased, the partial pressure on the permeate side of the membrane is further reduced, causing a greater impurity driving force and permeation flux without significantly affecting the hydrocarbon product permeation driving force.

This process is particularly applicable to the use of hollow fiber membranes since the conventional hollow fiber membrane unit need only be modified slightly or not at all to carry out the process.

In normal situations where appreciable partial pressure driving forces are maintained across the membrane, the cross-flow geometrical configuration driving force differs from the true theoretical countercurrent driving force by less than a few percent. However, in cases where limited partial pressure driving forces are available due to external constraints but it is still desirable to utilize a semi-permeable membrane device to effect a separation, the disadvantage of the cross-flow geometry becomes significant. It may therefore be desirable to utilize a hollow fiber membrane geometry which more closely approaches true countercurrent permeation driving forces.

Figure 2:
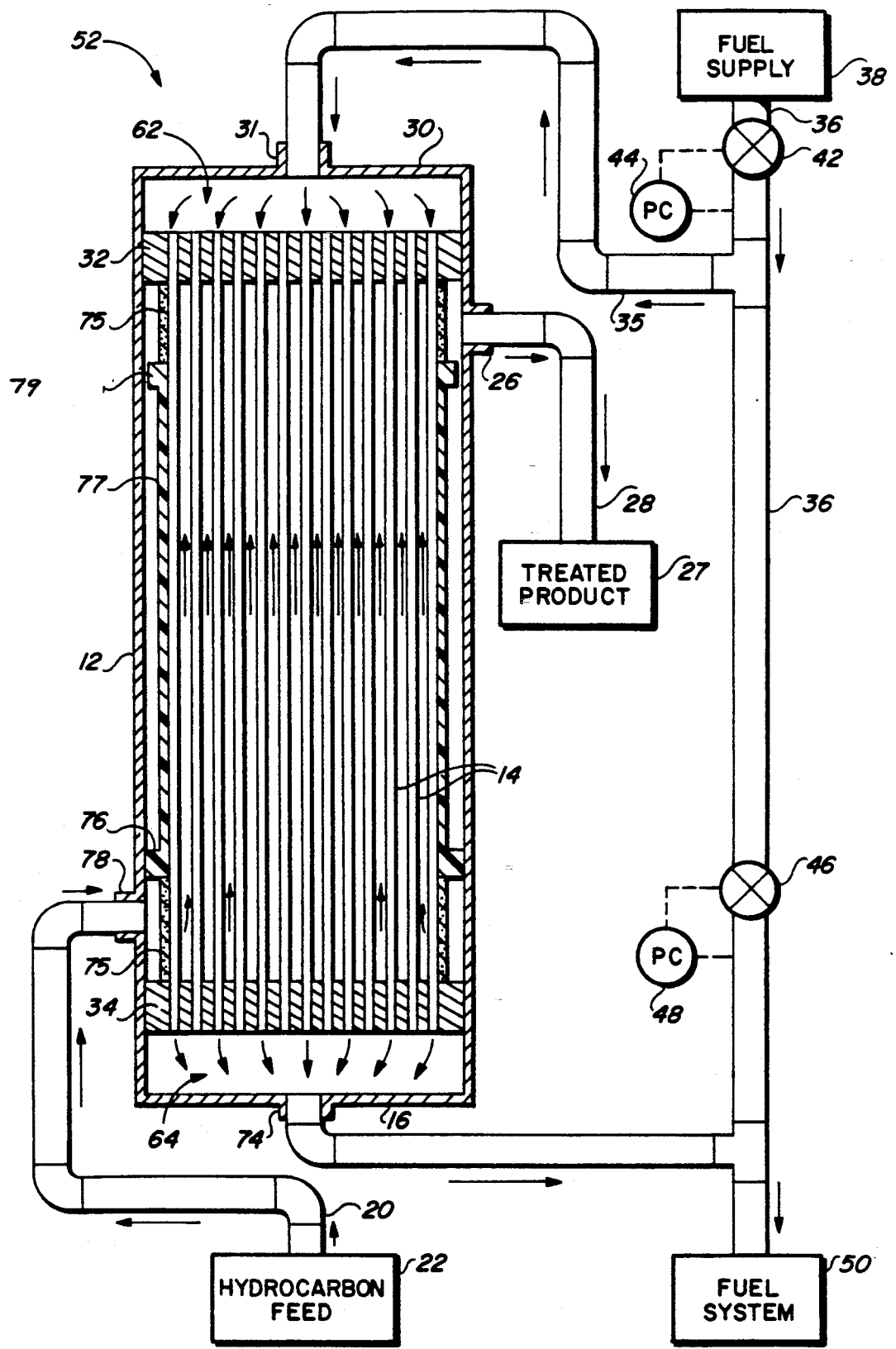
FIG. 2 is a longitudinal sectional view of another type of membrane unit in a similar system to that of FIG. 1, arranged so that countercurrent rather than crossflow extraction may occur.

A modified arrangement designed to operate in this manner is illustrated in FIG. 2, wherein like reference numerals to those used in FIG. 1 denote like elements. The unit 52 comprises a shell 12 which contains discs or plates 32 and 34 spaced from the end walls 30 and 16 of the shell to create chambers or header spaces 62 and 64. Hollow fiber membranes 14 are mounted in the disks 32 and 34 so that their ends communicate with the chambers. Porous wraps 75 located adjacent the discs 32 and 34 hold the end portions of the membrane fibers and allow hydrocarbon to enter the interior of the fiber bundle. A sealing ring 76, provided at the interior end of the lower porous wrap 75, and a non-porous wrap 77, extending upwardly from the sealing ring 76 and holding the central portion of the membrane fibers, prevent hydrocarbon fluid from short-circuiting the fiber bundle through the annular space between the shell 12 and the non-porous wrap 77. A non-sealing spacer ring 79 centralizes the bundle but will not allow pressure to build up in the annular space between the membrane bundle and the shell. An inlet 78 is provided in the side wall of the shell 12 adjacent the lower porous wraps 75, and the outlet 26 is adjacent the other porous wrap 75.

In use, the process is similar to the process described in connection with FIG. 1. The hydrocarbon feed mixture enters the shell 12 through inlet 78 and flows through the adjacent porous wrap 75 to the interior of the fiber bundle and axially along the hollow fibers 14. It then flows through the other porous wrap 75 to the annular space between the fiber bundle and the shell from which treated product flows out the outlet 26. The sweep gas enters the unit through the inlet 31 located in the end wall 30 of the unit and flows inside the hollow fiber membranes 14, sweeping along the permeated impurities and out the outlet 74. The purging action and dilution of the impurities are the same as explained in connection with FIG. 1.

Figure 3:
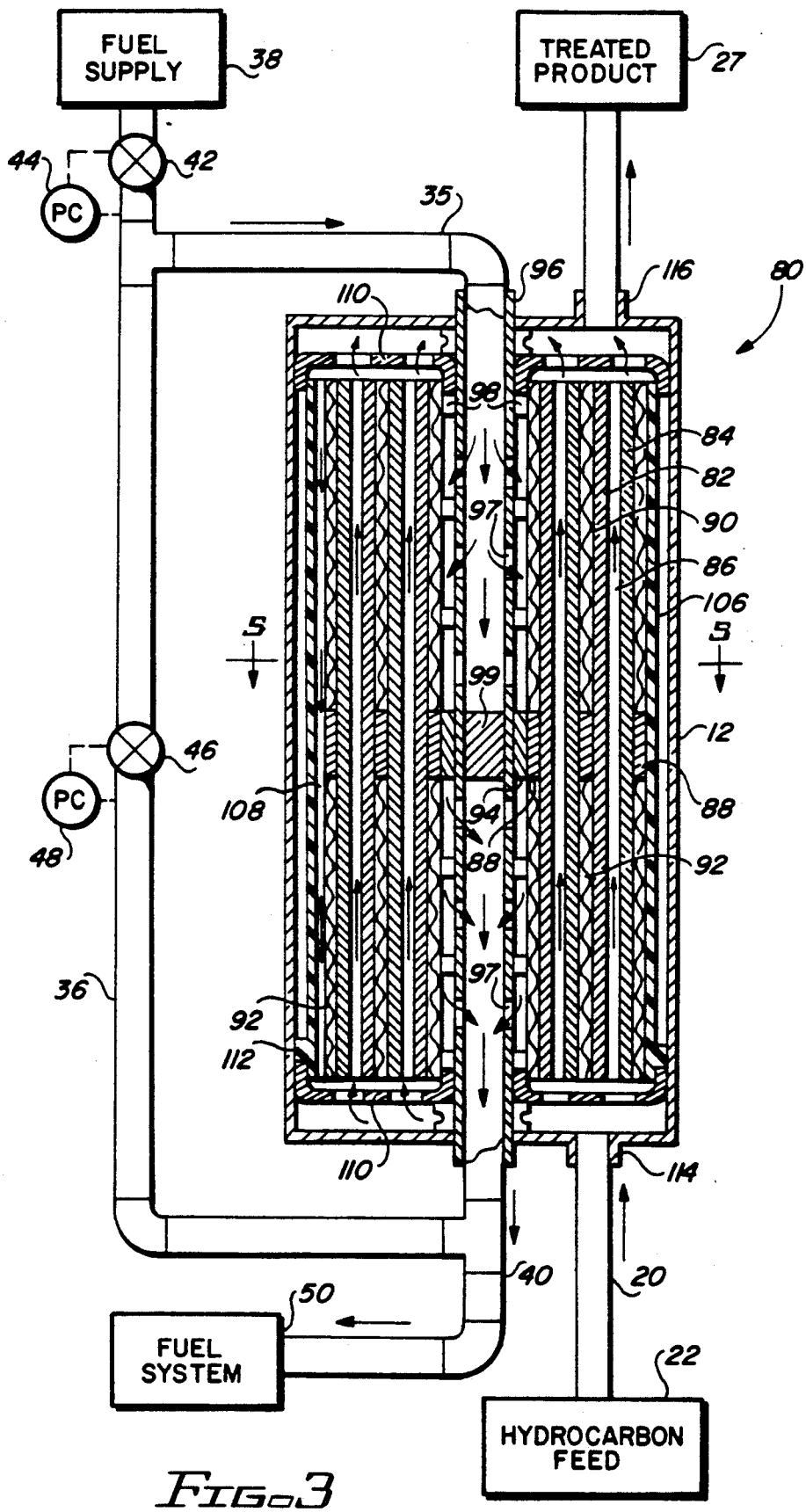
FIG. 3 is a longitudinal sectional view of a further type of membrane unit utilizing spirally wrapped spaced layers of sheet membranes.

As an alternative to the use of hollow fiber membranes, spirally wrapped sheet membranes can be used to permit impurities to be separated from hydrocarbon mixtures in accordance with the process of the invention. Referring to FIG. 3, the membrane unit 80 comprises a container or shell 12 in which spaced sheet membranes 82 and 84 are located in spirally wrapped form between the inlet tube 96 and the side wall of the shell. The sheet membranes 82 and 84 are alternately spaced apart by a spacer layer 86 and a spacer layer comprised of sealer strip 88 centrally located between spacer layers 90 and 92 in end-to-end fashion.

Figure 4:
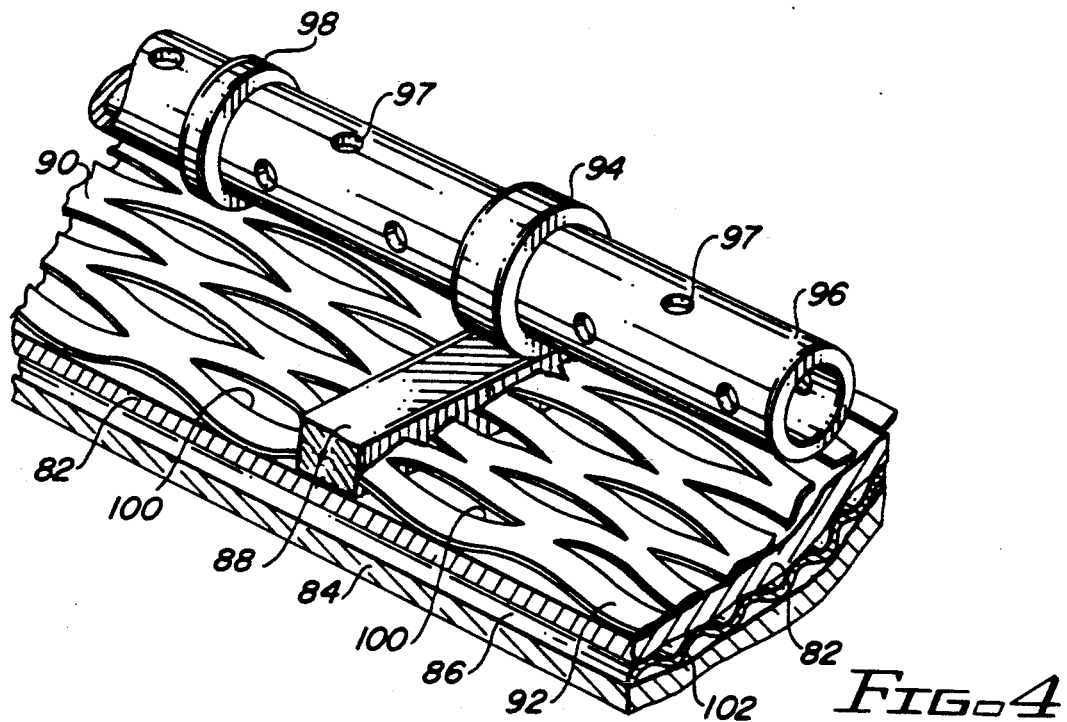
FIG. 4 is an enlarged pictorial view of a portion of the unit of FIG. 3.

The membrane configuration illustrated in FIG. 3 is formed by spirally winding the stacked layers shown in FIG. 4 about a sealing spacer ring 94, mounted on perforated tube 96 at a location midway between the ends of the container 12, and about other spacer rings 98, mounted on the perforated tube at spaced locations from the spacer ring 94 and from each other. The sealing spacer ring 94 is located opposite a central sealing plug 99, shown in FIG. 3, in the perforated tube 96. The layer adjacent the spacer rings is comprised of the spacer layers 90 and 92 separated by the sealing strip 88, which is aligned with the sealing spacer ring 94. It can be seen that the spacer layers 90 and 92 are in the form of slit-expanded flexible sheets, with the spaces through the slits 100 forming a flow path in a direction transverse to the perforated tube 96. The layer 86 separating the membranes 82 and 84 is in the form of a corrugated sheet which, while holding its corrugated shape, is nevertheless sufficiently flexible to be wrapped around the tube 96. In such an arrangement the corrugations 102 run parallel to the perforated tube 96 so that the troughs between them form a flow path parallel to the tube 96. Alternatively, the layer 86 could also be constructed of slit-expanded sheets, with the spaces through the slits forming the flow path parallel to the tube 96.

Figure 5:
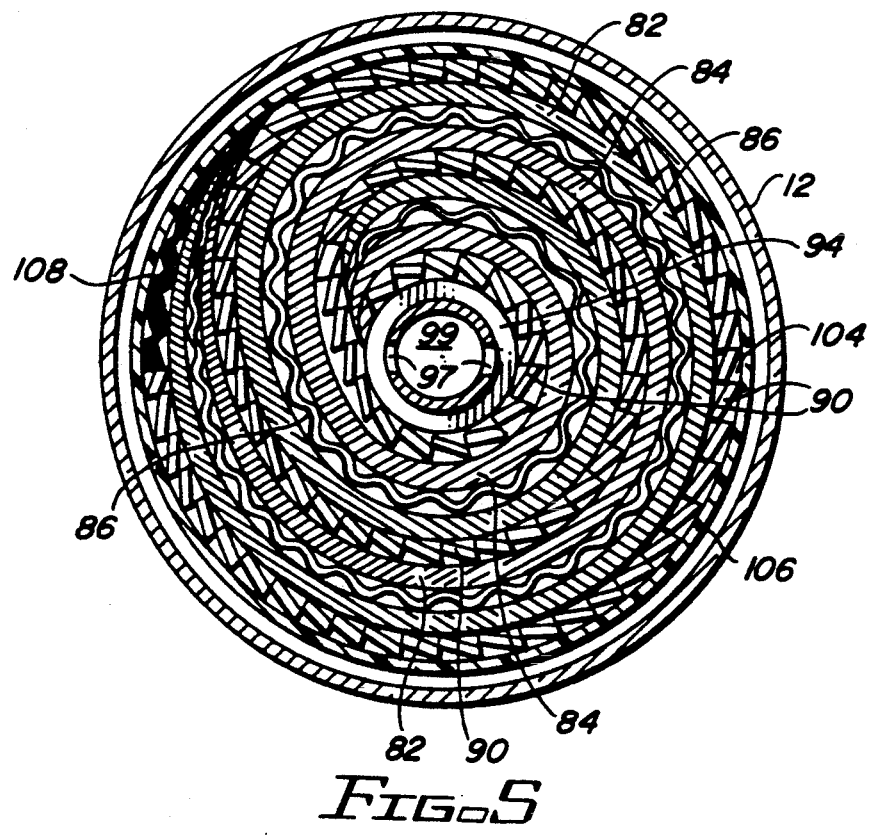
FIG. 5 is a transverse sectional view taken along line 5—5 of FIG. 3.

Referring back to FIG. 3 and also to FIG. 5, in the illustrated arrangement both the innermost spacer layer and the outermost spacer layer of the spirally stacked membrane unit are comprised of the slit-expanded sheets 90 and 92 and the intervening spacer ring 88. This configuration is achieved by making this spacer layer longer than the other layers in the stack so that it overlaps the membrane 82 as shown at 104. The spirally wound stack is contained within an impermeable wrap 106 which seals the outer surface of the spirally wound stack and consolidates the spiral stack into a unit. Extending beyond the end of the outer layer 104 of the spiral stack and inside the impermeable wrap 106 for the length of the spiral stack is another layer 108 similar in construction to the slit-expanded layer 90. For the purpose of illustration, the layer 108 has been shown as being blackened so as to be more readily distinguishable from the layer 90. As shown in FIG. 5, the layer 108 extends for only a short arcuate distance.

The spiral stack is held between perforated end caps 110 containing central openings through which the tube 96 passes, thereby centralizing the bundle within the shell 12. Sealing ring 112 prevents the short-circuiting of hydrocarbon fluid around the bundle through the annular space between the bundle and the shell 12.

In operation, hydrocarbon product enters the unit through inlet 114 and flows through the perforations in the end caps 110, continuing axially between the membrane sheets 82 and 84 within the spacer layer 86 while impurities in the stream are diffused through the membranes. Treated product exits through the perforations in the other end cap 110 and through the outlet 116. The sweep gas entering through tube 96 flows out the perforations 97 located above the sealing plug 99 and into the spacer layer 90, which causes the sweep gas to take a spirally outward path until it reaches the layer 108. The resulting mixture of permeate and sweep gas then flows axially through the spacer layer 108 into the spacer layer 92, through which it flows in a spirally inward path, returning to the perforated tube 96 below the sealing plug 99. The permeate and sweep gas mixture collected in the bottom half of the tube 96 flows to fuel system 50 via conduit 40. The conduit and valve system of FIG. 3 is similar to that shown in FIGS. 1 and 2, with like reference numerals denoting similar elements.

The benefits of the invention are many and significant. By utilizing a sweep gas to purge and dilute the permeate, the total back pressure on the permeate side of the membrane is increased to the point where there is sufficient pressure to deliver the permeate without the use of a compressor, which is quite significant given the high cost of a compressor of the necessary size. Because the use of a sweep gas dilutes impurities to a greater extent than it dilutes hydrocarbon product vapor, the driving force for the impurities is also greater, resulting in more efficient removal of impurities from the hydrocarbon product stream than is obtained in conventional membrane operation. Another benefit of this phenomenon is that it improves membrane selectivity. Thus the invention can provide better purification with the same membrane area that is required in the conventional process or can provide the same purification as the conventional process but with reduced membrane area and reduced product losses.

By utilizing fuel gas for the sweep and delivering the mixture of sweep gas and permeate to the fuel system of the plant in which the treatment operation is located, the hydrocarbon vapor included in the permeate can be burned for its fuel value. The process of the invention is especially effective in fractionation plants where large amounts of fuel are used to separate hydrocarbon liquid products into components by distillation where it can replace the amine process pretreatment for removal of carbon dioxide prior to or after fractionation.

If the process should be used to remove sulfur compounds or other impurities which are not desirable to be burned in the fuel and emitted to the atmosphere, any conventional process to selectively remove these sulfur compounds from the fuel stream prior to its use may be employed. Alternatively, in plants where a claus-type sulfur recovery process or sulfur tailgas clean-up processes are operating, the fuel and permeate mixture can be routed directly to these units.

It should now be appreciated that the invention need not be limited to all the specific details of the described embodiments, but that changes to certain features of the embodiments which do not alter the overall basic function and concept of the invention may be made without departing from the spirit and scope of the invention defined in the claims.

What is claimed is:

1. A process for separating gaseous impurities from a hydrocarbon mixture, comprising the steps of:
    contacting one side of a semi-permeable membrane with a flowing stream of the hydrocarbon mixture, the membrane being selectively permeable to the impurities desired to be separated so as to allow such impurities to diffuse through the membrane; and
    purging impurities which have diffused through the membrane by contacting the other side of the membrane with a stream of sweep gas flowing in a direction which is countercurrent or crosscurrent to the direction of flow of the hydrocarbon mixture;

the stream of sweep gas diluting and reducing the partial pressure of the impurities on the permeate side of the membrane to thereby increase the driving force of the impurities across the membrane while at the same time increasing the total back pressure on the membrane;

the ratio of the molar flow rate of the sweep gas to the molar permeation rate of impurities removed from the hydrocarbon mixture being at least 2 to 1, thereby reducing the partial pressure of the impurities on the permeate side of the membrane and correspondingly increasing the driving force and permeation flux of the impurities across the membrane, while allowing the back pressure to be significantly greater than atmospheric pressure;

the partial pressure of the impurities being decreased to such an extent that there is no need for a compressor in the fluid system containing the membrane unit, and the total back pressure on the membrane being increased to a point where permeate may be delivered by said back pressure directly to another station in the fluid system.

2. A process for separating gaseous impurities from a hydrocarbon mixture, comprising the steps of:

contacting one side of a semi-permeable membrane with a flowing stream of the hydrocarbon mixture, the membrane being selectively permeable to the impurities desired to be separated so as to allow such impurities to diffuse through the membrane;

purging impurities which have diffused through the membrane by contacting the other side of the membrane with a stream of sweep gas flowing in a direction which is countercurrent or crosscurrent to the direction of flow of the hydrocarbon mixture;

the stream of sweep gas diluting and reducing the partial pressure of the impurities on the permeate side of the membrane to thereby increase the driving force of the impurities across the membrane while at the same time increasing the total back pressure on the membrane;

the permeate containing vaporized hydrocarbon liquid and the sweep gas comprising fuel gas; and adding the permeate mixture of fuel gas, gaseous impurities and vaporized hydrocarbon to the fuel system of a hydrocarbon treatment plant.

3. The process of claim 2, wherein the pressure of the fuel gas sweep is sufficient to maintain flow through the membrane unit and into the fuel system.

4. A membrane unit for use in separating gaseous impurities from a fluid mixture by contacting one side of a semi-permeable membrane with a flowing stream of the fluid mixture, the membrane being selectively permeable to the impurities desired to the separated to permit such impurities to diffuse through the membrane to exit from the other side of the membrane, the membrane unit comprising:

a membrane container having opposite ends;

a plurality of sheet membranes mounted in the container, the membranes extending from a point spaced from one end of the container to a point spaced from the other end thereof;

the membranes being spaced from each other to form a first flow path between surfaces of said one side of the spaced membranes and a second flow path between the surfaces of the other side of the membranes;

a first inlet in the container for introducing the fluid mixture into the first flow path adjacent one end of the membranes;

a first outlet in the container for withdrawing treated fluid mixture from the first flow path adjacent the opposite end of the membranes;

a second inlet in the container for introducing sweep gas into the second flow path adjacent said opposite end of the membranes;

a second outlet in the container for withdrawing a mixture of sweep gas and gaseous impurities from the second flow path adjacent said one end of the membranes;

the spaced membranes being spirally wound about a central axis and being maintained in spaced condition by spacing means, the first flow path being between the spaced membranes in a direction substantially parallel to the central axis, the spacing means permitting flow in said direction, and the second flow path including a spiral path formed by spacing means between the surfaces of said other side of the membranes, the spiral path being transverse to the central axis;

a conduit located centrally of the spirally wound membranes and being connected to the second inlet and the second outlet;

means in the conduit intermediate the length thereof for blocking flow through the conduit;

means for blocking the spiral path intermediate the length of the membrane unit;

the conduit having openings therein on either side of the means for blocking flow through the conduit, the openings connecting with the spiral flow path;

a further flow path connecting the spiral paths on either side of the spiral path blocking means, whereby sweep gas introduced through the conduit will move spirally outwardly toward the further flow path in areas of the membrane unit upstream of the blocking means and spirally inwardly toward the conduit in areas of the membrane unit downstream of the blocking means.

* * * * *